United States Patent [19]

Sohval et al.

[11] Patent Number: 4,637,040

[45] Date of Patent: Jan. 13, 1987

[54] PLURAL SOURCE COMPUTERIZED TOMOGRAPHY DEVICE WITH IMPROVED RESOLUTION

[75] Inventors: A. Robert Sohval, Brookline, Mass.; David Freundlich, Haifa, Israel

[73] Assignee: Elscint, Ltd., Haifa, Israel

[21] Appl. No.: 818,892

[22] Filed: Jan. 14, 1986

Related U.S. Application Data

[63] Continuation of Ser. No. 518,121, Jul. 28, 1983.

[51] Int. Cl.⁴ .............................................. G01N 23/06
[52] U.S. Cl. ......................................... 378/9; 378/10; 378/19
[58] Field of Search ................. 378/9, 10, 19, 901; 382/6, 41; 364/414; 358/111

[56] References Cited

U.S. PATENT DOCUMENTS

| | | | |
|---|---|---|---|
| 3,250,916 | 5/1966 | Rogers | 378/41 |
| 3,452,232 | 6/1969 | Seki et al. | 378/41 |
| 3,819,968 | 6/1974 | Haberrecker | 378/134 |
| 4,002,917 | 1/1977 | Mayo | 378/19 |
| 4,010,370 | 3/1977 | Lemay | 378/12 |
| 4,072,875 | 2/1978 | Webley | 378/125 |
| 4,128,781 | 12/1978 | Flisikowski et al. | 378/4 |
| 4,135,095 | 1/1979 | Watanabe | 378/10 |
| 4,149,079 | 4/1979 | Ben-Zeev et al. | 378/9 |
| 4,171,476 | 10/1979 | Waltham | 378/9 |
| 4,178,511 | 12/1979 | Honnsfield et al. | 378/901 |
| 4,206,360 | 6/1980 | Le May | 378/12 |
| 4,239,972 | 12/1980 | Wagner | 378/9 |
| 4,266,136 | 5/1981 | Duinker | 378/901 |
| 4,315,154 | 2/1982 | Weigl et al. | 378/115 |
| 4,384,359 | 5/1983 | Franke | 378/9 |
| 4,555,760 | 11/1985 | Op de Beck et al. | 378/901 |

FOREIGN PATENT DOCUMENTS 406067 11/1924 Fed. Rep. of Germany ........ 378/41

Primary Examiner—Craig E. Church
Assistant Examiner—John C. Freeman
Attorney, Agent, or Firm—Sandler & Greenblum

[57] ABSTRACT

An apparatus for examining a body by means of penetrating radiation. The apparatus has a source of penetrating radiation for transmitting radiation through a body, and a detector array disposed to detect the radiation after passage through the body. Radiation beams emitted by the source traverse a plurality of paths through the body and are detected by the detector. The source has at least two distinct point sources for emitting radiation. The distinct point sources of radiation alternately emit radiation. The detector array can be a reduced array of detectors which subtends less than the full reconstruction circle diameter. A method is provided for increasing the spatial resolution in a CT scanner by increasing the sampling density by interleaving radiation beams emitted by the radiation source between adjacent radiation beams continuously as the source and detectors are rotated about the body.

34 Claims, 15 Drawing Figures

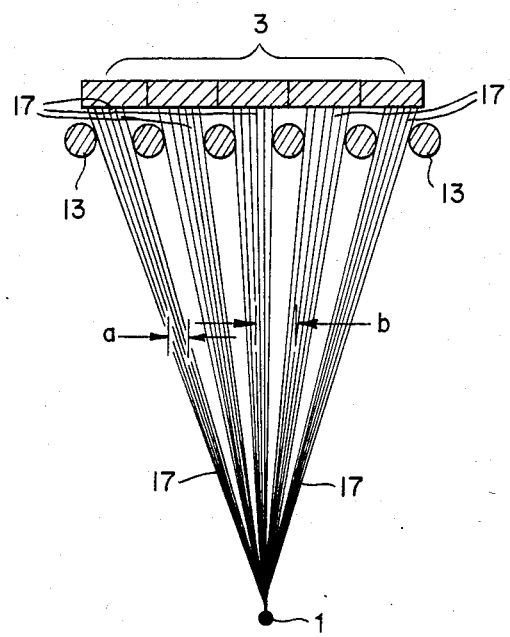
FIG. 10.
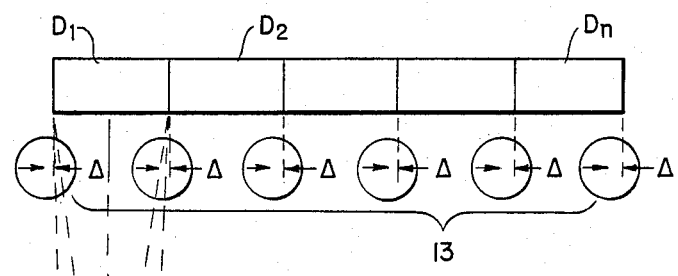
FIG. 11.
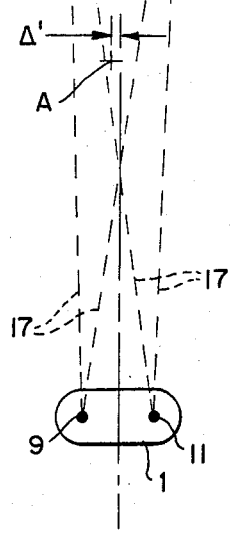

PLURAL SOURCE COMPUTERIZED TOMOGRAPHY DEVICE WITH IMPROVED RESOLUTION

This application is a continuation of application Ser. No. 518,121, filed July 28, 1983.

The present invention relates to systems for examining a body by means of penetrating radiation such as X-radiation.

BACKGROUND OF THE INVENTION

CT scanners have become an established technique for acquiring essentially planar cross-sectional images of a live body anatomy or the interior of an inanimate object. There are three essential features sought in high-quality CT scanners: (1) high spatial resolution; (2) high-contrast resolution for tissue differentiation; and (3) high scan speed to minimize blurring from patient motion and to perform dynamic studies in which several scans are acquired in rapid succession. High spatial resolution is generally characteristic of images acquired in translate-rotate CT scanners whereas high scan speeds are generally characteristic of rotate-rotate CT scanners.

The intrinsic spatial resolution of a CT scanner is determined primarily by two factors: (1) effective beam width at the center of the object, and (2) sampling frequency. The effective beam width is a function of the focal spot size, the detector aperture width, and the magnification factor (defined as the X-ray tube-object separation v. the X-ray tube-detector separation); this is true regardless of whether the scanner is operated in the translate-rotate or rotate-rotate mode. Assuming the effective beam width has been optimized, the sampling frequency becomes all important. As to sampling frequency, the difference between translate-rotate and rotate-rotate acquired data is critical.

In rotate-rotate scanners, the sampling frequency, as well as the effective detector aperture, are limited by the size of detectors provided. This is due to the intrinsic geometry of a rotate-rotate scanner in which the X-ray source and the bank of detectors are fixed in relation to one another, and are both rotated about the object. As a result, the geometry of rotate-rotate scanners restricts the smallest possible sampling distance to the distance between the detectors, and the sampling frequency to once per beam width. According to the Nyquist criterion, however, the sampling frequency should be at least twice as great, i.e., two or more measurements per beam width. Because the geometry of the rotate-rotate scanner does not satisfy the Nyquist criterion, image-degrading aliasing artifacts may be caused by high contrast, high spatial frequency structures in the image. In order to avoid aliasing artifacts, the data must be pre-filtered by combining measurements in adjacent detector channels to attenuate the high spatial frequencies having a period less than two beam widths. In this manner, a new beam width is effected, which is twice as large as the actual beam width, so that the Nyquist criterion is satisfied. Thus, the intrinsic spatial resolution capability of the rotate-rotate scanner, as measured by its beam width, must be degraded by a factor of two to prevent aliasing artifacts.

By contrast, in a translate-rotate scanner, the gantry to which the X-ray tube and detectors are fixed may be indexed in increments smaller than or equal to half the beam width, satisfying the Nyquist criterion. Thus, aliasing artifacts are eliminated while preserving the intrinsic spatial resolution of the system.

Furthermore, in rotate-rotate scanners, the above-described lack of flexibility in adjusting the sampling frequency would make post-patient collimation to reduce the beam width futile because the distance between the detectors is constant and narrow beams would not improve the ultimate spatial resolution beyond the limit set by the sampling frequency.

By comparison, in translate-rotate scanners, post-patient collimation may be used to reduce beam width and to improve spatial resolution, because the gantry may be indexed in correspondingly smaller increments to maintain a sampling frequency of at least twice per beam width.

To compensate for limitations in sampling frequency imposed by the one-ray-per-detector relationship inherent in conventional rotate-rotate scanners, some rotate-rotate scanners use a technique of offsetting the center of rotation to simulate an increase in the sampling rate. Using this technique, if the center of rotation of the gantry (i.e., its iso-center) is offset by a distance equal to one-fourth the effective beam width at the iso-center, two views taken 180° apart will be shifted by one-half of the detector pitch. It can be seen that, using this technique, after the gantry has rotated 180°, the rays from the diametrically opposed views interleave such that the sampling density is effectively doubled and spatial resolution is improved. However, this technique only works in the ideal case where there is no patient motion. If the object to be scanned moves by a fraction of a millimeter during the few seconds required for gantry rotation, registration will be lost, and proper interleaving of the views will no longer be achieved. This can introduce aliasing artifacts which degrade the image. Thus, although this technique simulates doubling the sampling frequency at the center of the object, it does not totally absolve rotate-rotate type scanners from the above-described deficiencies resulting from limited sampling frequencies.

Another method of increasing the sampling density is to collect data from the detectors in a given position, and then to shift the detectors laterally (or rotate them about the iso-center) by half of the detector-to-detector pitch while the X-ray source is in the same position, and collect additional data; this results in interleaving of the data collected in the first 180° rotation with that collected in the second 180° rotation such that the sampling frequency is effectively doubled. These data are then processed in the usual way (i.e., filter and back-projection) to form a CT image. However, the mechanics of moving the detectors but not the X-ray source during a scan as described above is inconvenient in rotate-rotate scanners, and would operate to defeat the advantage of simple mechanics which characterizes rotate-rotate CT scanners.

U.S. Pat. No. 4,149,079 discloses a system for increasing data density to obtain a more accurate reconstruction in a system having a reduced detector array, i.e., a system in which the apical angle of the fan beam is less than the apical angle of the reconstruction circle. This patent provides for either rotating or linearly displacing the fan beam relative to the fixed center of the reconstruction circle to obtain a second data set after a first data set has been obtained during a complete rotation. This system is, therefore, disadvantageous in that it requires two separate rotations and also mechanical means for shifting the fan beam.

U.S. Pat. No. 4,266,136 discloses a CT apparatus which also uses a reduced detector array. The source emits a fan beam of radiation having an apical angle which subtends less than the diameter of the reconstruction circle so that only one-half of the object slice is irradiated at any given time. Processing means convert the data produced by the detectors into parallelized profile signals suitable for processing by a conventional reconstruction algorithm. This system is disadvantageous in that the acquired data density is insufficient to satisfy the Nyquist criterion and hence poor reconstructed images will be provided thereby.

These above-described prohibitive sampling limitations which are present with rotate-rotate scanners have led to the development of a modified rotate-stationary scanner having a stationary array of detectors. In such systems, a complete circle of detectors is rigidly mounted around the patient area. The X-ray source is located inside or outside the detector area, and data is acquired as the X-ray source is rotated. Although rotate-stationary systems having stationary detectors achieve flexibility in sampling, they create new limitations so that, in the end, their intrinsic spatial resolution and overall clinical performance roughly equal that of the original rotate-rotate arrangement. The most notable problem with rotate-stationary systems is efficiency; i.e., they are costly due to the large number of detectors required. In addition, rotate-stationary systems have structural difficulty in eliminating scatter radiation and associated high background noise; this results in poor contrast resolution. Further, the common rotate-stationary design, which has the X-ray source mounted inside the ring of detectors, is burdened by the difficulty of optimizing the tube-object v. object-detector separation because both the X-ray source and the object must be confined within a detector ring which should be kept as small as possible so that the number of detectors does not become excessive. Another disadvantage in rotate-stationary systems is increased skin dose to the patient due to the short tube-object distance. These problems are severe enough to have prompted the development of a scanner in which the X-ray source rotates around the object outside the detector ring to optimize the distance between the tube, the object and the detectors. Such systems, however, are burdened by excessive mechanical complexities because, in order to allow the unimpeded beams to fall on the detectors on the opposite side of the scanned object, the detectors closest to the tube must be moved out of the field of radiation while the tube rotates. This is accomplished by nutating the detector ring.

It is therefore an object of the present invention to provide a new and improved computerized tomography method and apparatus which substantially overcomes the above-described deficiencies in the prior art.

SUMMARY OF THE INVENTION

The present invention overcomes the above-described problems associated with improving the intrinsic spatial resolution in a rotate-rotate or similar scanner. Moreover, the present invention provides improved spatial resolution in translate-rotate, rotate-stationary, fully stationary strobed source scanners, or any other source-detector configuration where the present invention may be implemented.

According to the present invention, an apparatus for examining a body by means of penetrating radiation such as X-radiation includes a source of penetrating radiation for transmitting radiation through a body under examination, the source including at least two distinct point sources of radiation, detector means for detecting the radiation after passage through the body, mens for causing radiation emitted by the source to traverse a plurality of paths through the body and to be detected by the detector means, and means for causing the distinct point sources to alternately emit radiation. The distinct point sources are preferably under computer control. The source can include a target electrode for emitting radiation in response to a beam of electrons impinging thereon and deflection means for deflecting the electron beam between at least two distinct focal spots on the target electrode. Further, the source can alternatively include an X-ray tube having at least two filaments, each filament including a distinct point source of radiation. The source can also alternatively include at least two X-ray tubes, each X-ray tube including a distinct point source of radiation. The source can include either a stationary anode or a rotating anode.

A post-patient collimator can also be provided. The collimator may be a high-resolution pin collimator. The source and detector means can be mounted on a rotatable gantry. The detector means can be a plurality of individual detectors disposed substantially uniformly along an arc on the gantry. The collimator means can be a corresponding plurality of collimators, with the center of each collimator being aligned with the center of a detector. Means can further be provided for offsetting the iso-center of the gantry by a distance equal to one-eighth the effective pitch of the detectors at the iso-center of the gantry. Alternatively, the center of each collimator can be offset from the center of a corresponding detector by one-eighth the detector pitch, and means can be provided for offsetting the iso-center of the gantry rotation by a distance equal to one-fourth the effective detector pitch at the iso-center.

In one embodiment, the source includes means for transmitting a fan beam of radiation and each transmitted fan beam has an apical angle $\alpha$ which is less than the apical angle $\beta$ which defines the reconstruction circle. Preferably $\alpha$ is approximately one-half of $\beta$ and is approximately in the range of 15° to 30°. The plurality of individual detectors is disposed on an arc on the gantry which subtends the apical angle $\alpha$. In one alternative, one of these individual detectors at the end of the detector array is substantially diametrically opposed relative to the source on the gantry such that the detector array is asymmetrically positioned relative to the gantry iso-center. In another alternative, the plurality of individual detectors can be disposed substantially symmetrically with respect to the iso-center of the gantry. Means for displacing the plurality of detectors with respect to the gantry iso-center can be provided to yield a system which can operate in either mode. This embodiment can also include means for offsetting the gantry iso-center with respect to the source and the detectors.

According to another embodiment of the present invention, an apparatus for examining a body by means of penetrating radiation such as X-radiation includes a source of penetrating radiation for transmitting radiation through a body, detector means disposed to detect the radiation after passage through the body, means for causing radiation emitted by the source to traverse a plurality of paths in the section and to be detected by the detector means, and shifting means for shifting the source with respect to the detector means. The means for shifting can comprise means for periodically shifting the source between at least two distinct positions with respect to the detector means as the source and the detector means are angularly displaced about the body.

According to the present invention, in a rotate-rotate CT scanner having a source of penetrating radiation for transmitting radiation through a substantially planar section of a body, detector means disposed to detect the radiation after passage through the body, means for angularly displacing the source and the detector about the body to cause radiation which traverses a plurality of coplanar paths in the section to be detected by the detector means, a method of improving the spatial resolution of images reconstructed by the scanner includes increasing the sampling density by interleaving radiation beams between adjacent radiation beams continuously as the source and the detector means are rotated about the body.

In summary, the present invention is advantageous in that it at least doubles the sampling density heretofore achievable in conventional rotate-rotate or similar scanners. As noted above, the present invention can also be used to increase the sampling density in translate-rotate, rotate-stationary, fully stationary strobed source systems, or other tomographic systems. It accomplishes this in the preferred embodiment by providing an X-ray tube having two or more focal spots which are displaced, preferably laterally, relative to one another. For example, in a tube having two focal spots, the displacement between focal spots is such that when the gantry rotates one-half the angular detector pitch, the second focal spot would occupy substantially the same azimuthal position as the first focal spot initially had occupied. This results in the interleaving of radiation beams emitted by the second focal spot between adjacent beams emitted by the first focal spot to achieve doubling of the sampling density. The two focal spots are operated in toggle mode with approximately fifty percent duty cycle. If an X-ray tube with three focal spots is used, the displacements between focal spots are such that three samples per beam width are obtained.

The ideal displacements between focal spots can be calculated according to the formula:

$$\Delta_s = R_s/R_d \times P(N+1/n)$$

where $R_s$=distance from the X-ray source to iso-center, $R_d$=distance from the detectors to iso-center, P=detector pitch, defined as the distance between the centers of adjacent detectors, n=number of focal spots and the number of samples per beam width, and N=0, 1, 2, ... Although the displacements calculated in accordance with the above formula are optimal, others are possible as well. As long as the displacements are close to those calculated above, substantial improvement in spatial resolution will be achieved. For the case of N=0, $R_s$=630 mm, P=1.6 mm, $R_d$=400 mm, and n=2, $\Delta_s$=1.26 mm.

According to the preferred embodiment with two focal spots, the focal spots can be alternately or successively switched within a period of approximately half a millisecond to a few milliseconds. This switching speed will result in the substantial elimination of aliasing artifacts due to patient motion. This affords a significant advantage over the prior art in which the gantry must rotate 180°, usually requiring a few seconds, to collect the additional views which are interleaved to compensate for aliasing.

Another advantage of the present invention is that pin collimators may be used to reduce the detector aperture and to thereby increase spatial resolution whereas, as noted above, in prior art rotate-rotate systems pin collimators are not useful. If the detector aperture is reduced by half, for example, there are two techniques for increasing the sampling density correspondingly in order to satisfy the Nyquist criterion. One technique is to use an X-ray tube with three or more focal spot positions. Although four positions are required to satisfy the Nyquist criterion, some improvement will be gained with three focal spots. The second technique is to offset the center of rotation (i.e., the iso-center) of the gantry and use an X-ray tube with two focal spots. The geometry of the iso-center offset and the high-resolution pin collimators can be effected in accordance with two different techniques. In one, the centers of the high-resolution collimators are aligned with the centers of the detectors, and the iso-center is offset by one-eighth of the effective detector pitch at the iso-center. In the other, the centers of the high-resolution collimators are offset from the centers of the detectors by one-eighth of the detector pitch while the iso-center is offset by one-quarter of the effective detector pitch at the iso-center. In both of these latter techniques, views taken 180° apart are interleaved to double the sampling density in the central region of the patient, thus satisfying the Nyquist criterion. The ability to use pin collimators and increased sampling frequency to improve spatial resolution represents a substantial improvement over prior art rotate-rotate scanners, in which spatial resolution is limited to the sampling density.

Yet another advantage of the present invention is that, instead of requiring a detector array with a full arc of detectors, i.e., with the detectors located along a circular arc having its center essentially diametrically opposed to the X-ray source where the arc subtends the entire reconstruction circle diameter such that the detector array can receive a fan beam of about 40° to 50° from the source as with conventional rotate-rotate CT scanners, a reduced arc of detectors, i.e., with the detectors on an arc which subtends less than the reconstruction circle diameter such that, for example, the detector array can receive a fan beam approximately in the range of 15° to 30°, can be employed, resulting in reduction in cost. In one embodiment, the reduced array is asymmetrically disposed so that the detector at one end of the arc is essentially diameterially opposed to the X-ray source, while in another embodiment, the reduced array is symmetrically disposed relative to the iso-center. A bimodal system can be achieved by providing means for displacing the semi-array of detectors on the gantry, thus allowing shifting to occur between an asymmetric and a symmetric configuration. The required number of detectors may be reduced by half, or by any other desired practicable fraction, while still achieving satisfactory spatial resolution, by the use of an x-ray tube having two or more focal spots. Although conventional rotate-rotate CT scanners can still reconstruct an image based upon 360° of data even after reduction of the number of detectors by one-half, such a scanner will have reduced spatial resolution; this is because in such a scanner, spatial resolution is sample frequency bound and quarter-ray offset of the gantry iso-center cannot be used because that technique requires a full arc of detectors. However, if such a scanner is provided with an x-ray tube having two or more focal spots which alternately emit radiation according to the present invention, the sample frequency is doubled and a two-fold improvement in spatial resolution is achieved. A 360° scan is still required.

The spatial resolution of a scanner with a multiple focal spot x-ray tube with a reduced number of detectors as described above would be the same as a conventional scanner using a full arc of twice as many detectors and a conventional x-ray tube having a single focal spot. For such a scanner according to the present invention, fewer aliasing artifacts arising from patient motion will occur because the time duration between interleaved samples is milliseconds, corresponding to the time between switching between focal spots, whereas the time duration between interleaved samples in conventional scanners is seconds, because interleaving to acquire the additional data occurs only after the gantry has rotated through 180°. When using a reduced array of detectors, unnecessary radiation dose can be eliminated by providing a collimator between the X-ray source and the patient to reduce the apical angle of the transmitted fan beam which passes through the patient to correspond to the reduced size of the detector array.

BRIEF DESCRIPTION OF THE DRAWINGS

Embodiment of the present invention are shown by way of example in the accompanying drawings, wherein:

FIG. 10 illustrates the use of high-resolution collimators to increase the spatial resolution; and FIG. 11 illustrates a second embodiment using high-resolution collimators to increase the spatial resolution;

DETAILED DESCRIPTION OF THE INVENTION

Figure 1:
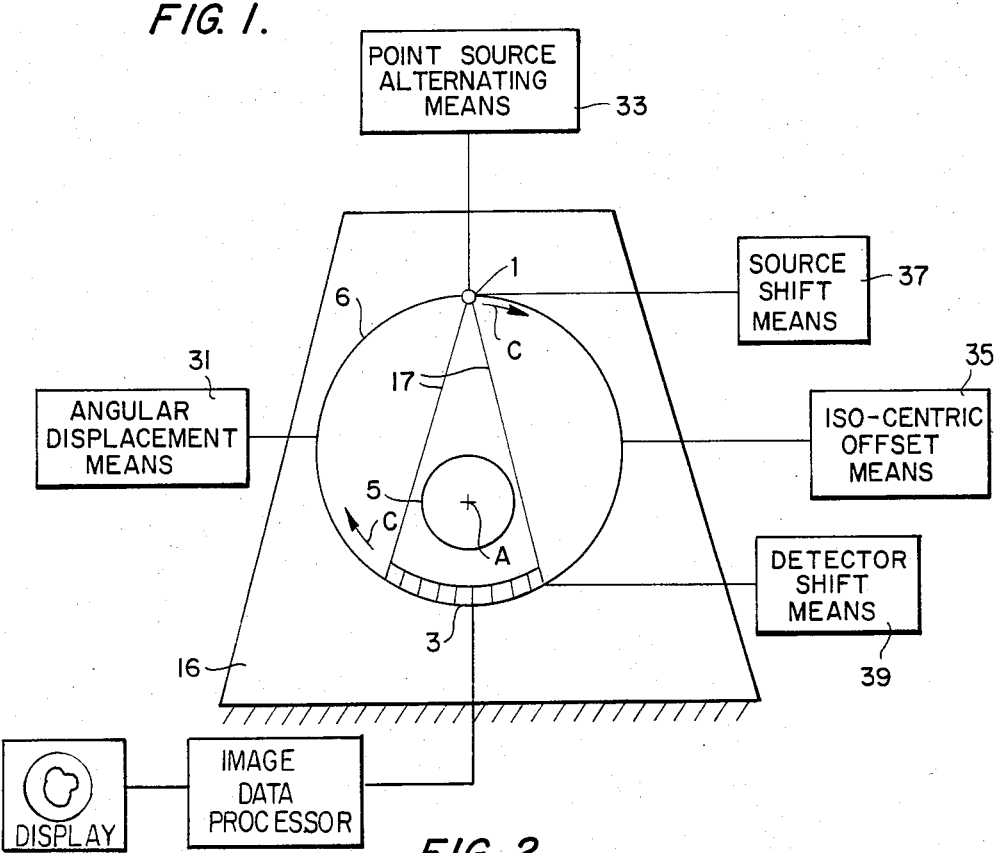
FIG. 1 illustrates a rotate-rotate CT scanner according to the present invention.

Referring now to FIG. 1, reference numeral 1 illustrates a source of penetrating radiation, such as an X-ray source, for transmitting radiation through a substantially planar section of a body, and reference numeral 3 illustrates a plurality of individual detectors which are disposed substantially uniformly along an arc on a rotatable, substantially circularly-shaped gantry, illustrated by reference numeral 6, which, in turn, is preferably mounted on support member 16. Detectors 3 are disposed substantially evenly-spaced preferably along an arc near the perimeter of the gantry. Data is acquired as the gantry, with source 1 and detectors 3 mounted thereon, is rotated in a continuous rotational sweep about the patient 5. The center of rotation of the gantry, i.e., its iso-center, is represented by "A". Reference numeral 17 illustrates a radiation beam which is emitted by source 1. Radiation beam 17 is shown as a fan beam of radiation lying in a substantially planar section of the body under examination. Each fan beam 17 emitted by source 1 originates substantially from a distinct point source within source 1. The arrows "C" represent the direction of rotation of the system. Source 1 includes at least two distinct point sources of radiation, as illustrated schematically in FIG. 4.

In FIG. 1, reference numeral 31 refers to means for angularly displacing the source and the detectors about the body 5 to cause radiation to traverse a plurality of coplanar paths in the aforementioned planar section and to be detected by detectors 3. Means 31 can comprise means for angularly displacing the gantry. Reference numeral 33 refers to means for causing the at least two point sources of radiation to alternately emit radiation. Means 33 can comprise means for causing the point sources to alternately emit radiation at a frequency whose period is equal to the time required for the gantry to rotate through an angle equal to the effective detector pitch at iso-center given by an angle formed by two lines connecting the iso-center of the gantry with the center of adjacent detectors disposed on the gantry. Alternatively, this period can be multiplied by N, where N equals 2, 4, 8, 16 . . . .

Reference numeral 35 refers to means for offsetting the iso-center "A" of gantry 15 with respect to source 1 and detectors 3.

Reference numeral 37 refers to shifting means for shifting source 1 with respect to detectors 3. Shifting means 37 can include means for periodically shifting the source between at least two distinct positions with respect to the detectors as the source and the detectors are angularly displaced about body 5. Reference numeral 39 refers to means for displacing the detectors on the gantry. Means 39 can include means for displacing the detectors between a first position at which the detectors are asymmetrically disposed with respect to the iso-center and a second position at which the detectors are symmetrically disposed with respect to the iso-center. Means 39 is preferably used with respect to a semi-array of detectors, as discussed in detail below.

The geometry of conventional rotate-rotate scanners limits the smallest possible sampling distance to the distance between two adjacent detectors, thus limiting the intrinsic spatial resolution capability of such systems to twice the distance between two detectors. In other words, the sampling distance effectively equals the beam width. The consequence of this sampling frequency is that the spatial resolution of a rotate-rotate scanner is only half as good as is theoretically possible. This is shown by the Nyquist theorem which requires that there be at least two samples per beam width to obtain maximum spatial resolution.

Figure 2:
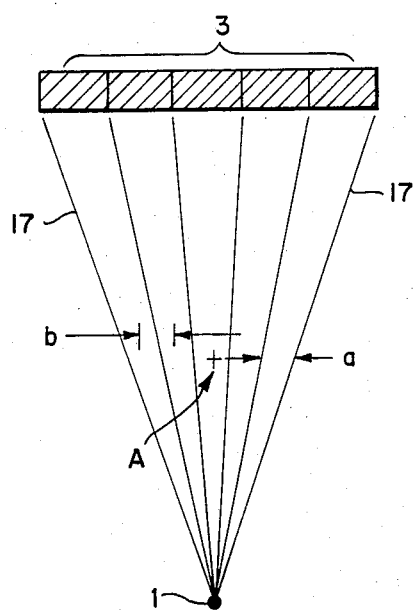
FIG. 2 illustrates the spatial resolution achievable in a conventional rotate-rotate scanner, showing why the Nyquist criterion causes reduction by a factor of two of the theoretical spatial resolution.

FIG. 2 illustrates why the Nyquist criterion causes reduction by a factor of two in theoretical spatial resolution in a conventional rotate-rotate CT scanner. In this figure, "a" represents the beam width of the radiation beam transmitted by X-ray source 1, and "b" represents the sampling distance or pitch. According to the Nyquist criterion, sample interval "b" should be less than or equal to half of the resolution or beam width "a"; i.e., "b" must be less than or equal to a/2. If "b" is less than a/2, then spatial resolution is equal to "a". If "b" is greater than a/2, then to avoid aliasing artifacts, the spatial resolution must be degraded, and it consequently will be greater than "a". For the case where b=a, as in a conventional rotate-rotate CT scanner, the spatial resolution is about equal to 2b (and hence also 2a because b=a).

Figure 3:
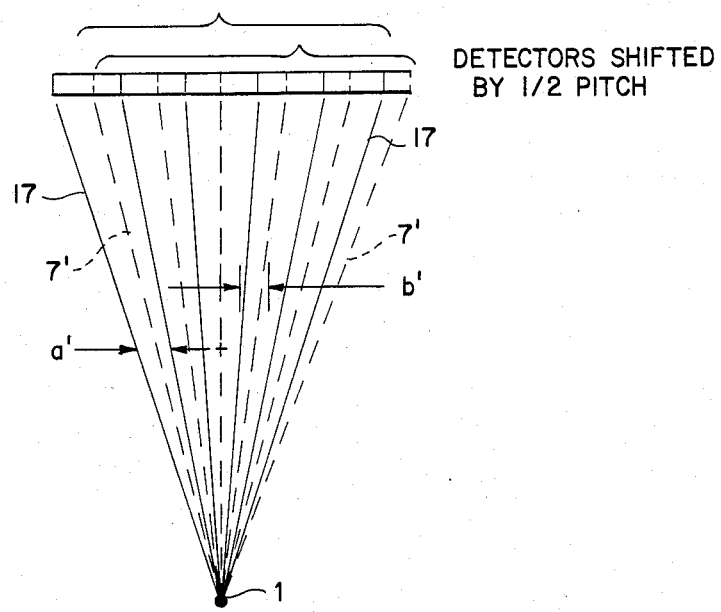
FIG. 3 illustrates shifting the detectors to increase the sampling density.

FIG. 3 illustrates the technique of shifting the detectors by one-half pitch to increase the sampling density. The shifted detectors are represented by dashed lines and reference numeral 3'. In FIG. 3, a' represents the beam width and b' represents the sampling distance or pitch. Relative to FIG. 2, a'=a, and b'=b/2=a/2. So now, with the detectors shifted by one-half pitch, there is no aliasing because the Nyquist criterion is satisfied, and the spatial resolution equals "a". The resolution is therefore twice as great as is shown in FIG. 2.

Figure 4:
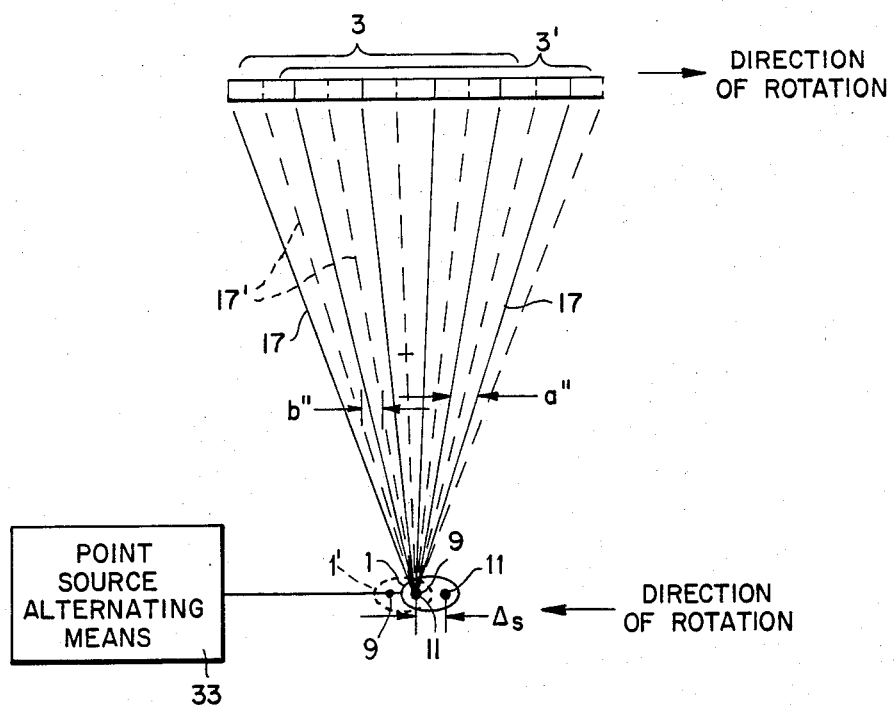
FIG. 4 illustrates shifting the focal spot to increase the sampling density.
Figure 15:
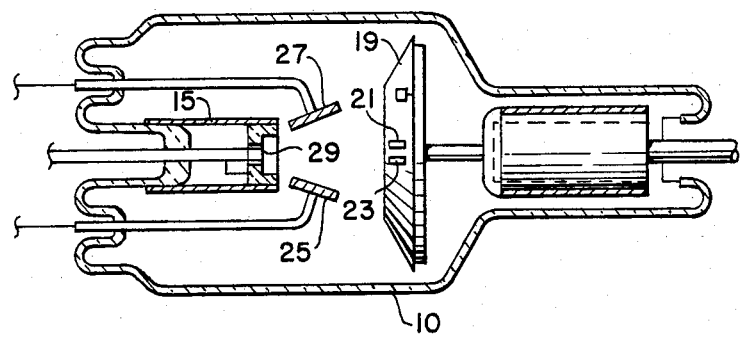
FIG. 15 illustrates the use of deflection electrodes to deflect the electron beam between alternative distinct focal spots on a target electrode.

FIG. 4 illustrates radiation source 1 in the form of an X-ray source, which includes two distinct point sources of radiation 9 and 11. Point sources 9 and 11 can be provided by a single X-ray tube having a pair of filaments. Alternatively, they can be provided by a radiation source 1 having a pair of X-ray tubes, each tube including a distinct point source of radiation. Also alternatively, they can be provided by deflection means for deflecting an electron beam between at least two distinct focal spots on a target electrode, as shown in FIG. 15. Means 33 are provided for causing the distinct point sources of radiation 9 and 11 to alternately emit radiation. It should be noted that source 1 can be provided with two or more distinct point sources which may be caused to alternately emit radiation. Alternate shifting of the point source of radiation, or focal sot, from position 9 to position 11 in X-ray source 1 provides an increase in the sampling density. In FIG. 4, X-rays are emitted from focal spot position 9 while detectors 3 are at position 3. X-rays continue to be emitted from focal spot position 9 as the gantry rotates one-half the angular detector pitch until detectors 3 are at position 3' and focal spot 11 occupies the same location which focal spot 9 had occupied initially. At this point, X-rays are emitted from focal spot 11 as the gantry continues to rotate another one-half detector pitch. After the gantry has rotated a complete detector pitch, X-rays are once again emitted from position 9. This cycle is repeated for the duration of the scan.

The displacement between focal spots 9 and 11 which is required in order to achieve a second focal spot which occupies the same azimuthal position as the first focal spot initially had occupied when the detectors have been shifted by one-half of the detector pitch can be obtained by the following formula:

$$\Delta_s = R_s/R_d \times P(N + 1/2)$$

where $R_s$=the distance from the X-ray source to the iso-center of the gantry, i.e., the center of rotation of the gantry, $R_d$=the distance from each detector to the iso-center, P=the detector pitch defined as the distance between the centers of adjacent detectors, and N=0, 1, 2, .... For N=0, $\Delta_s = R_s/R_d \times P/2$.

It is seen that by providing multiple focal spots as described above, the sampling frequency is at least doubled since radiation beams 17' can be interleaved between adjacent radiation beams 17 continuously as the radiation source and detectors are rotated about the iso-center. Using a multi-focal spot system, this interleaving is accomplished independently of any alteration of the spatial relationship between source 1 and detectors 3 because the fixed relationship between X-ray source 1 and detectors 3 on the gantry is maintained throughout a full 360° revolution of the gantry. Further, the radiation beams are interleaved as the radiation source and the detectors are rotated about the patient; the interleaving is accomplished by alternately emitting radiation from the multiple point sources of radiation or focal spots. Radiation is alternately emitted between focal spots at a frequency whose period is preferably equal to the time required for the gantry to rotate through the detector pitch. This period can also be multiplied by N, where N equals 2, 4, 8, 16 ....

Alternatively, according to the present invention, source 1 shown in FIG. 1 can be made to emit radiation from more than one distinct point source by providing shifting means 37 for shifting source 1 with respect to detector means 3. The shifting means preferably includes means for periodically shifting source 1 between at least two distinct positions with respect to detector means 3. This causes each detector to receive radiation from multiple point sources as the gantry is rotated. The shifting means can be any conventional means for shifting the location of source 1 relative to the detector array 3.

The increased sampling density provided by multi-focal spots, as well as alternative data-acquisition schemes, can be understood by referring to FIGS. 5-9 in which the data are presented in polar coordinates.

Figure 5:
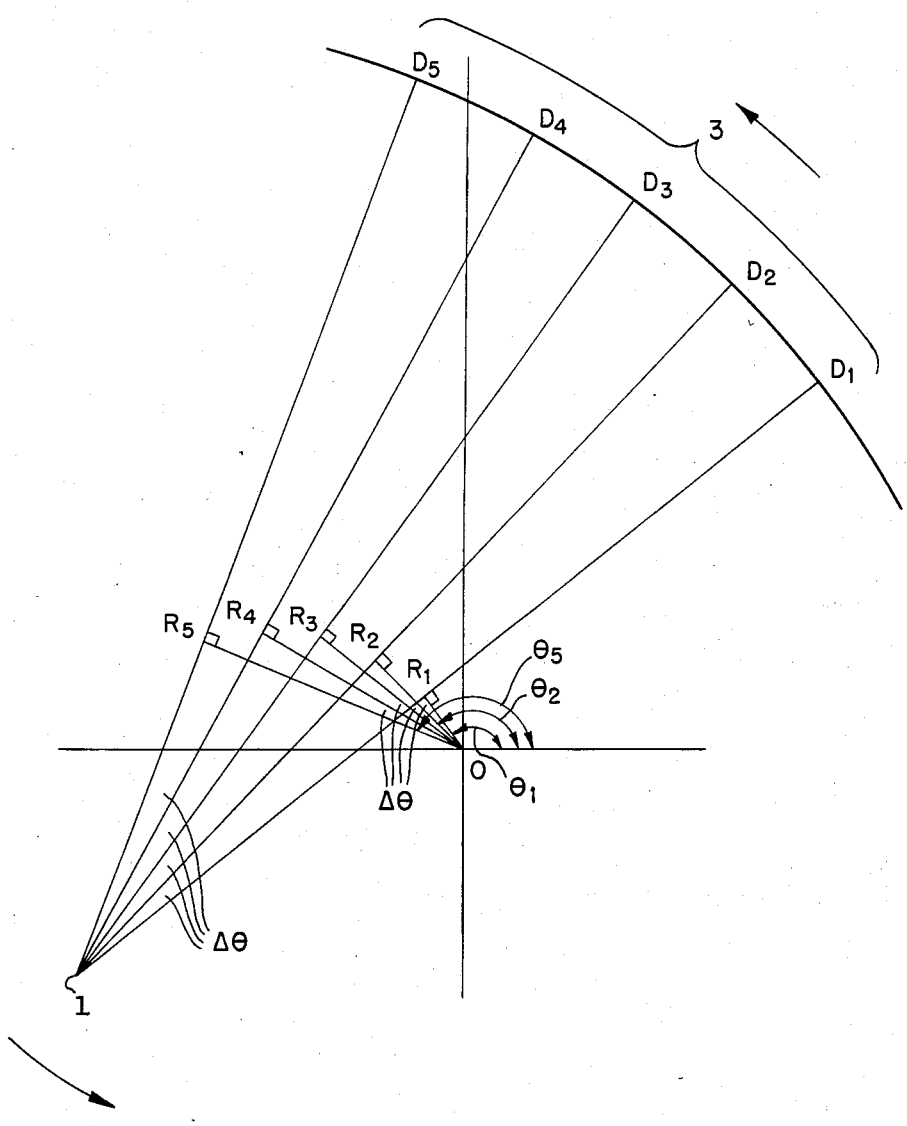
FIG. 5 illustrates the geometry of a rotate-rotate scanner in polar coordinates.

Referring to FIG. 5, the spatial location of every X-ray measurement can be labelled in polar coordinates, (r,θ), relative to the iso-center "A". For example, the ray formed by X-ray source 1 and detector $D_1$ is defined by the polar coordinates (r,θ) where r equals the distance $R_1$−0, and θ is $\theta_1$. The next ray in the fan, formed by source 1 and detector $D_2$, has polar coordinates (r,θ) where r equals the distance $R_2$−0 and θ is $\theta_2$. Thus, it can be appreciated that r is proportional to the detector number and that, in a given fan, θ for each ray increases by Δθ where Δθ is the angle subtended by the detector pitch as seen by the source 1.

Figure 6:
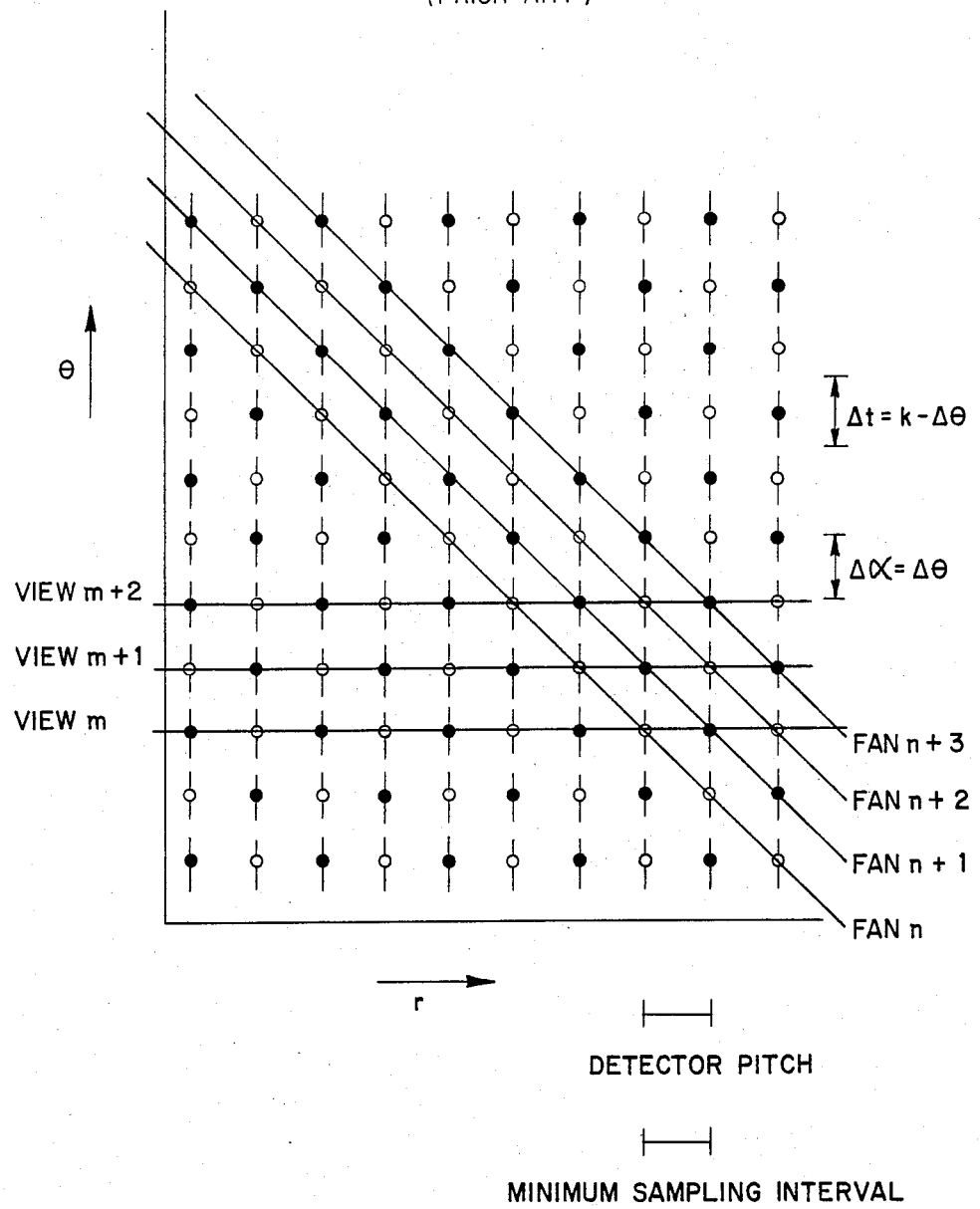
FIG. 6 illustrates a polar-coordinate map of the data collected by a conventional rotate-rotate scanner with a single X-ray source.

The data collected by a conventional rotate-rotate CT scanner with a single X-ray source are shown in FIG. 6. The data from each fan lies along a diagonal line in this r−θ diagram since θ and r both change proportionally to detector number. Data collected in a given fan are shown by either open or closed circles, and this symbol alternates on successive fans.

Since the gantry rotates during data acquisition, each measurement extends over a small range of values of θ. The circles (either open or closed) indicate the average value of θ, and the vertical lines above or below the circle indicate the range in θ over which data are collected.

After the data have been acquired, the data may be combined in new groupings defined as "views" which have constant angle $\theta$. Thus, the data in each set are essentially parallel rays. In the case shown in FIG. 6, the acquisition time $\Delta t$ for each fan is the time required by the gantry to rotate by $\Delta\theta$.

Thus, $\Delta t$ is proportional to $\Delta\theta$; $\Delta t = k\Delta\theta$, where $1/k$ is proportional to the rotation speed. Also, the angular sampling which is given by the angular distance between views $\Delta\alpha$ is equal to $\Delta\theta$. The minimum sampling interval equals the detector pitch resulting in degraded spatial resolution, since the Nyquist criterion is not satisfied, as previously described.

Figure 7:
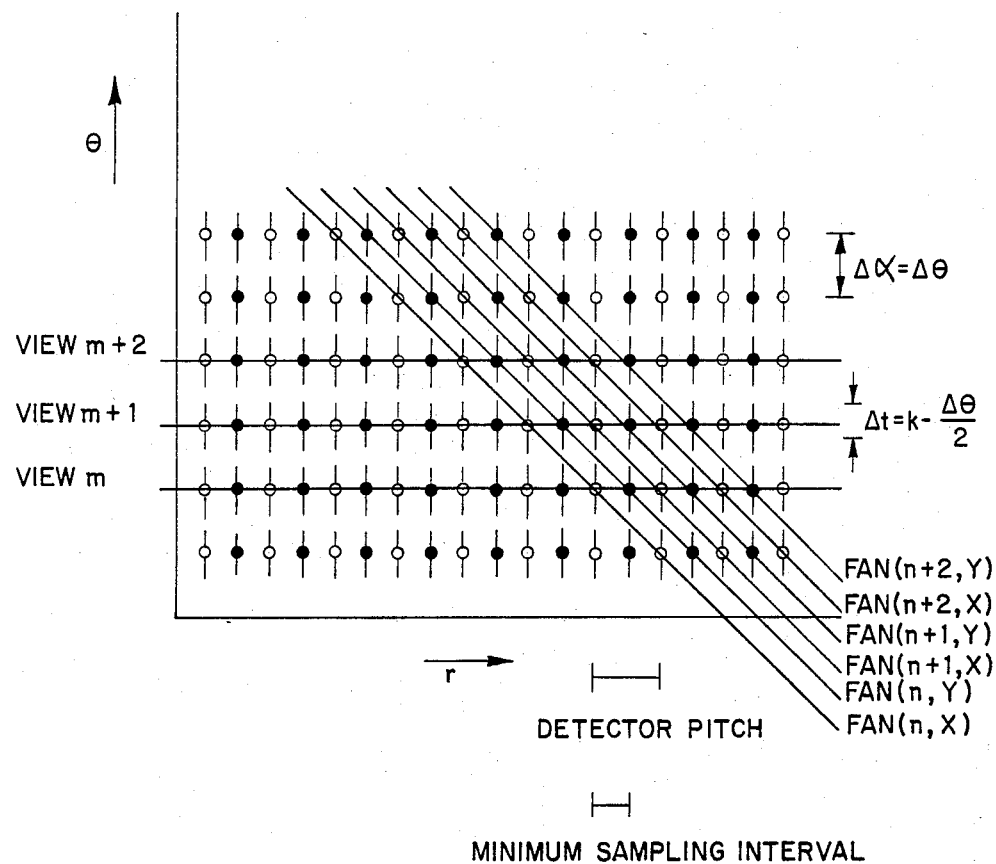
FIG. 7 illustrates a polar-coordinate map of the data collected by shifting the focal spot to increase the sampling density.

Using the X-ray source with two focal spots which are separated by a distance given by the formula above and which alternately emit radiation results in the arrangement shown in FIG. 7. Fan data collected when the focal spot is in position x(y) are shown with open (closed) circles. By halving the integration time and alternating between focal spots x and y, the data can be organized into views of constant $\theta$ separated by an angular distance $\Delta\alpha = \Delta\theta$. Most importantly, the sampling distance equals one-half the detector pitch, which satisfies the Nyquist criterion and results in much-improved spatial resolution.

Although this embodiment achieves parallel views, satisfies the Nyquist criterion, and yields substantially improved spatial resolution, it is characterized by a reduced data acquisition time, $\Delta t = (k\Delta\theta)/2$, since the focal-spot position is changed each time the gantry rotates half of the angular detector pitch. This shortened data acquisition time limits the quantity of detected X-ray flux and may reduce the signal-to-noise ratio, as well as requiring a more costly, higher-speed data-acquisition system.

Figure 8:
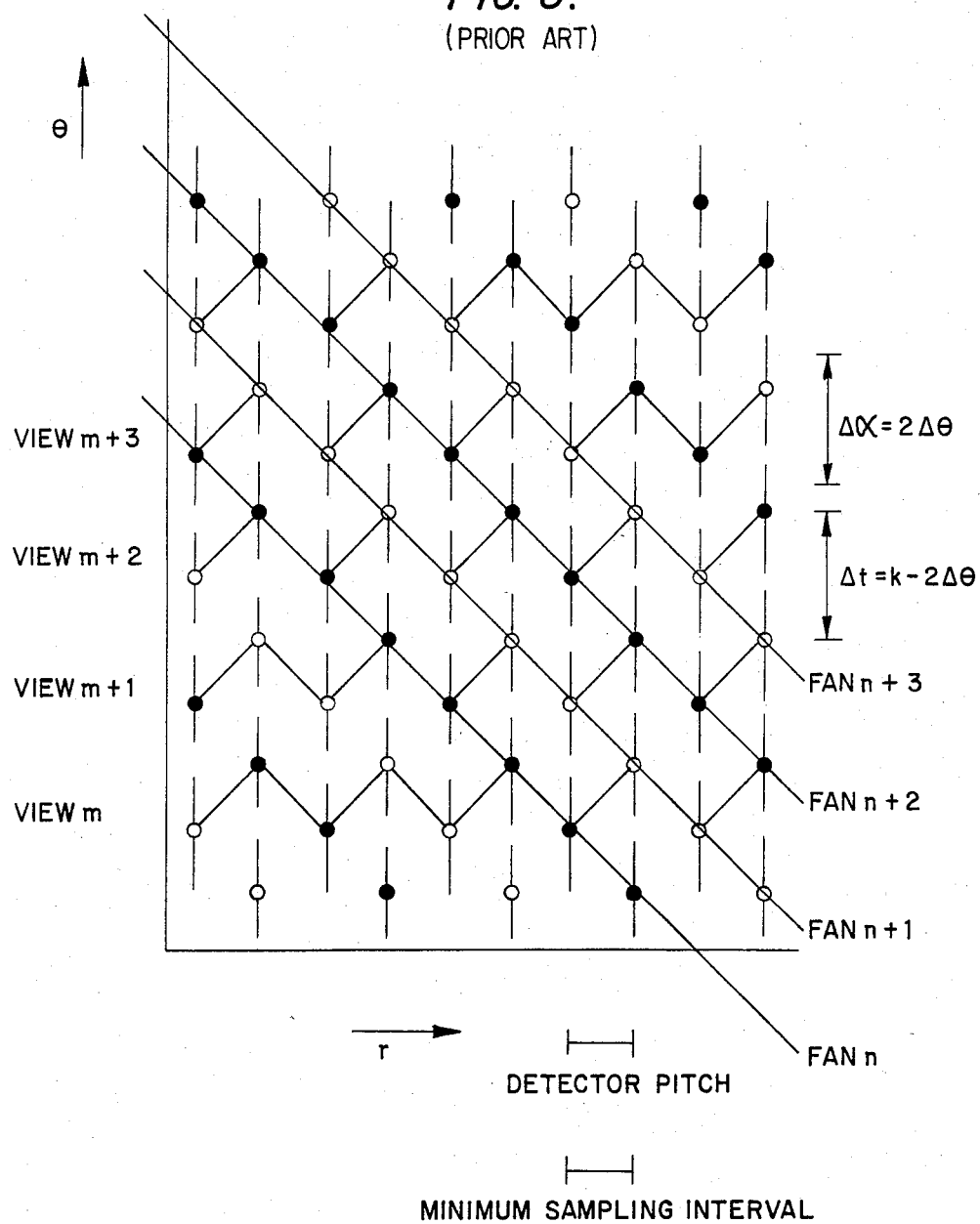
FIG. 8 illustrates a polar-coordinate map of the data collected by a conventional rotate-rotate scanner, extending the angular sampling distance and acquisition time.

This disadvantage may be overcome by increasing the acquisition time and angular sampling distance. FIG. 8 shows the $r-\theta$ diagram for a conventional rotate-rotate CT scanner with a single-focal-spot X-ray tube which rotates $2\Delta\theta$ per acquisition. In comparison to FIG. 6, the integration time is twice as long, and the angular distance $\Delta\alpha$ is twice as great, resulting in half as many total views. The minimum sampling distance equals the detector pitch, as in FIG. 6, which does not afford improved spatial resolution. In addition, it may be appreciated from FIG. 8 that the data cannot be organized into perfectly parallel views with constant $\theta$. This will result in a small loss of angular resolution, which, in turn, will slightly degrade spatial resolution at distances far from the iso-center, say, 200 mm. radius, where high spatial resolution is less important and is usually degraded for other reasons in CT scanners. However, the spatial resolution at the iso-center is not degraded in this scheme.

Figure 9:
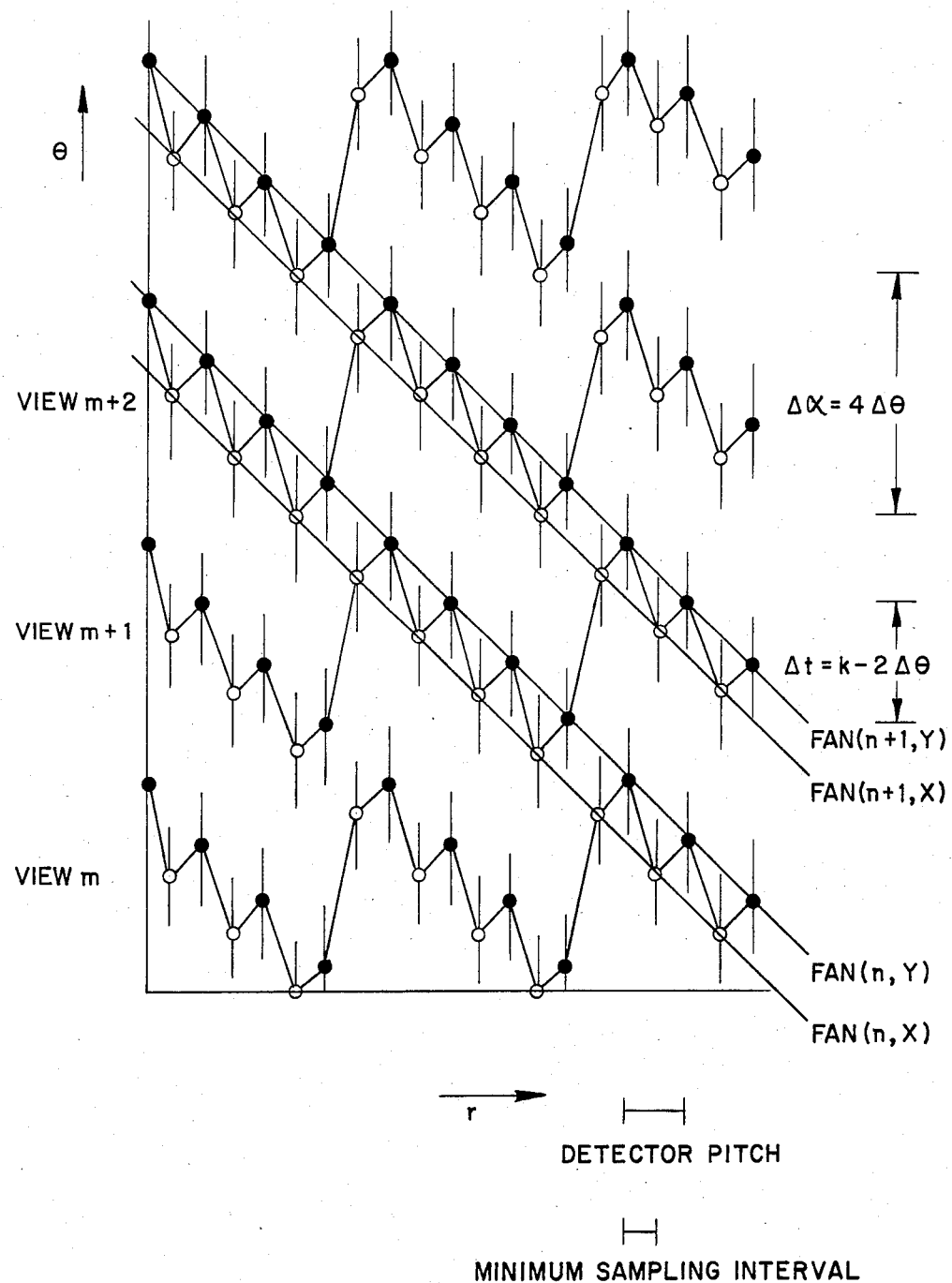
FIG. 9 illustrates a polar-coordinate map of the data collected by extending the angular sampling distance and acquisition time, and shifting the focal spot to increase sampling density.

Combining the greater data acquisition time with an X-ray source with two focal spots results in the $r-\theta$ diagram shown in FIG. 9. In this case, the longer acquisition time is achieved, $\Delta t = 2k\Delta\theta$, which is four times longer than the example in FIG. 7. The angular sampling distance is also four times greater, $\Delta\alpha = 4\Delta\theta$. This results in one-quarter the total number of views as in FIG. 7, thus significantly reducing the computational burden of image reconstruction without sacrificing image quality. As in FIG. 8, because the gantry rotates more than $\Delta\theta$ during acquisition, the data cannot be organized into perfectly parallel views with constant $\theta$. However, the resulting slight degradation in image quality will be confined to peripheral regions far from the iso-center. Use of the two focal spots x and y provides a minimum sampling distance equal to half the detector pitch, which satisfies the Nyquist criterion, and results in substantially improved spatial resolution, despite the longer acquisition time.

FIG. 10 illustrates the use of a high-resolution collimator 13 to reduce the detector aperture and increase spatial resolution. In the preferred embodiment, pin collimators 13 reduce the detector aperture and increase spatial resolution. In FIG. 10, a is fifty percent its value in FIGS. 4-6, and b = 2a, whereas the required value for the sample pitch is a/2. One solution is to use an X-ray tube with three or more focal-spot positions to increase the sampling density.

Alternatively, an x-ray tube with two focal spots can be used and the iso-center of rotation can be offset a small distance so that views taken 180° apart are interleaved to double the sampling density. The geometry of the iso-center offset and the location of the high-resolution pin collimators relative to the detectors are provided in two different embodiments according to the present invention. In one embodiment, the centers of the high-resolution collimators are aligned with the centers of the detectors, as shown in FIG. 10, such that pin beams 17' impinge substantially at the centers of detectors 3, and the gantry iso-center is offset by one-eighth of the effective detector pitch at the iso-center. In the other embodiment, as illustrated in FIG. 11, the centers of the high-resolution collimators 13 can be offset from the centers of the detectors $D_1$–$D_n$ by one-eighth of the detector pitch, such that pin beams which pass through collimators 13 impinge the detectors substantially at points which are offset by approximately one-eighth the detector pitch from the centers of the detectors, and the iso-center is offset by one-quarter of the effective detector pitch at the iso-center. As shown in FIG. 11, reference symbol "$\Delta$" represents the offset of the collimator centers relative to the detector centers which can be any desired practicable amount but is preferably one-eighth or one-quarter of the detector pitch. Reference symbol $\Delta'$ represents the offset of the gantry iso-center relative to the effective detector pitch at iso-center which also can be any desired practicable amount but is preferably one-fourth of the beam width at the iso-center. In the case of post-patient collimation to reduce the detector aperture to fifty percent, the required factor-of-four increase in sample frequency is achieved by dual focal spots ($\times 2$ sampling frequency) and one-eighth ray offset ($\times 2$ sampling frequency).

Figure 12:
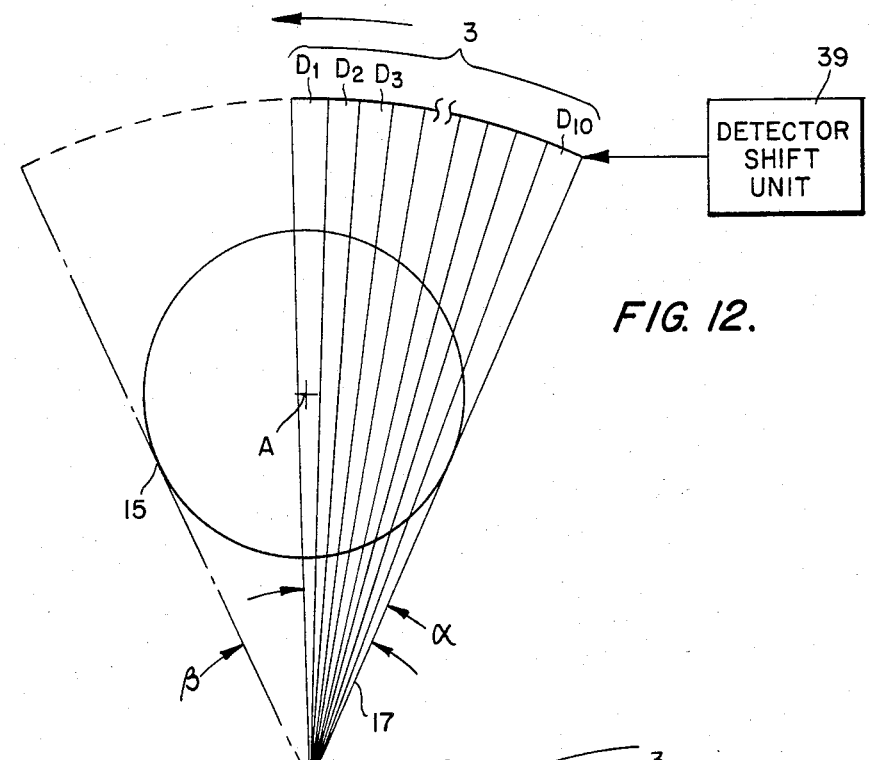
FIG. 12 illustrates a CT scanner employing an X-ray source having a fan beam having apical angle $\alpha$ which is less than the apical angle $\beta$ which defines the circle of reconstruction.

FIG. 12 illustrates another embodiment of the present invention utilizing a reduced detector array. In FIG. 12, detector means 3 is formed of a plurality of individual detectors represented by symbols $D_1$–$D_{10}$. X-ray source 1 has two distinct point sources of radiation, although any number of point sources greater than one can be provided. Reduced detector array 3 is mounted along a preferably substantially circular arc having its center at X-ray source 1.

In FIG. 12, reference numeral 15 refers to the reconstruction circle associated with a fan beam having an apical angle equal to $\beta$, where the apical angle is defined as the angle between the extremities of the fan beam. The extent of the detector array which is commensurate with such a fan beam is shown by the dashed lines to the left of reduced array 3. As shown, such a fan beam has a medial beam which passes through fixed iso-center "A" about which source 1 and detectors 3 are rotatable in the plane of the detectors. During one complete revolution of the source-detector assembly, the source will move in a circle concentric with fixed iso-center "A" and the fan beam having apical angle $\beta$ will sweep out an area, in the plane of the detectors, which is contained within circle 15. Circle 15 is coincident with iso-center "A" and its periphery is tangent to the beams defining the periphery of the fan beam centered as described above relative to the iso-center and having apical angle $\beta$. For a given scanner, the diameter of the reconstruction circle is directly related to the magnitude of the apical angle of the fan beams.

Fan beam 17 illustrated in FIG. 12 has an apical angle $\alpha$ which is less than $\beta$. Beam 17 is commensurate with reduced detector array 3, whereas a fan beam having apical angle $\beta$ is commensurate in scope with a full detector array extending as far as the dashed lines in FIG. 12. FIG. 12 shows $\alpha$ to be about 20°–25° and $\beta$ to be about 40°–50°. It should be noted that both $\alpha$ and $\beta$ can have other desired practicable values; preferably $\alpha$ will be in the range of 15°–30° and will equal substantially one-half the value of $\beta$. The apical angle of a fan beam can be changed by altering associated collimators or by altering the X-ray source.

It is apparent from FIG. 12 that the arc which contains reduced detector array 3 subtends less than the diameter of reconstruction circle 15. The detector array subtends the apical angle $\alpha$ of fan beam 17 emitted by X-ray source 1. This arc preferably subtends substantially one-half the diameter of circle 15, so that where $\beta$ equals approximately 40°–50°, $\alpha$ equals approximately 20°–25°. It should be noted, however, that $\alpha$ can be any desired practicable amount. In contrast, the detector array in conventional rotate-rotate CT scanners is disposed along an arc which subtends the entire reconstruction diameter and which usually corresponds to a maximum fan beam of about 40° to 50°. As shown in FIG. 12, X-ray source 1 is substantially diametrically opposed with respect to left-most detector $D_1$ on the gantry. In the preferred embodiment, means are provided for offsetting the iso-center of rotation of the gantry preferably by a distance equal to one-quarter of the detector pitch at iso-center. In the scanner shown in FIG. 12, detector array 3 is asymmetrically disposed relative to the iso-center of the gantry with end detector $D_1$ diametrically opposed to source 1.

Figure 13:
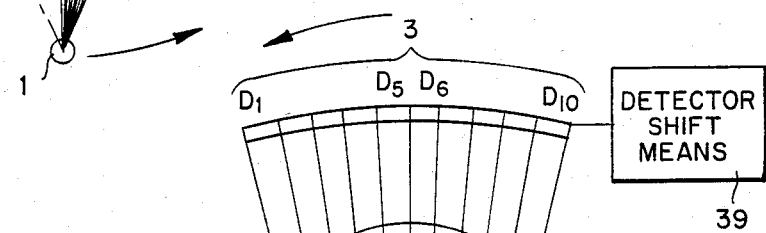
FIG. 13 illustrates a modification of the CT scanner of FIG. 12.

For imaging small diameter objects, such as heads, the half detector array on the apparatus shown in FIG. 12 can be shifted to a new position essentially symmetrically disposed with respect to the iso-center "A" as shown in FIG. 13. The midpoint between middle detectors $D_5$ and $D_6$ is substantially diametrically opposed to X-ray source 1 as shown. It should be noted that the fan beam 17 in FIGS. 12 and 13 does not subtend the entire reconstruction circle 15 but rather only approximately one-half thereof.

It should also be noted that where a reduced array of detectors is used, a pre-patient collimator (not shown) can be provided to reduce the apical angle of the fan beam to correspond to the reduced detector array and to thereby avoid unnecessary radiation dosage.

For high resolution scans of small object fields using the scanner shown in FIG. 13, a high resolution postpatient pin collimator may be used as illustrated in FIG. 11. The geometry of the iso-center offset and the location of the high-resolution pin collimators relative to the detectors can be provided in two different embodiments according to the present invention. In one, the centers of the high-resolution collimators are aligned with the centers of the detectors, and the iso-center is offset by one-eighth of the effective detector pitch at the iso-center. In the other, the centers of the high-resolution collimators are offset from the centers of the detectors by one-eighth of the detector pitch, and the iso-center is offset by one-quarter of the effective detector pitch at the iso-center. In the case of post-patient collimation to reduce the detector aperture to 50 percent, the required factor-of-four increase in sample frequency is achieved by dual focal spots ($\times 2$ sampling frequency) and one-eighth ray offset ($\times 2$ sampling frequency). In the preferred embodiment, means are provided for offsetting the iso-center of rotation of the gantry by a distance equal to one-quarter of the effective detector pitch at the isocenter while the centers of the collimators are offset from the centers of the detectors by one-eighth of the detector pitch.

The configuration shown in FIG. 13 with high-resolution pin-collimators as described above, is particularly adapted for scans of small objects such as heads, and yields the following advantages. First, higher sampling frequency, with accompanying increased spatial resolution, is achieved over conventional scanners. Second, faster scans are achieved over conventional scanners because rotation of about 205°, i.e., 180° plus fan beam (preferably about 25°), is sufficient instead of rotation of 360°. Third, high resolution pin collimators can be used to increase spatial resolution whereas, as noted above, in conventional rotate-rotate scanners having a single focal spot X-ray tube, pin collimators are ineffective to increase spatial resolution. Fourth, the scanner is less sensitive to patient motion, since the additional views to be interleaved are acquired within milliseconds, rather than seconds as in conventional scanners which must rotate 180° to acquire this data.

In FIGS. 12 and 13, reference numeral 39 refers to means for displacing detectors 3 on the gantry. This provides a bimodal capability wherein a single scanner can be adapted to operate alternatively in either mode illustrated in FIGS. 12 and 13. FIG. 12 shows detectors 3 in a first position at which the detectors are asymmetrically disposed with respect to iso-center "A" and FIG. 13 shows them in a second position at which they are symmetrically disposed with respect to the iso-center.

Where a pre-patient collimator for reducing patient dose by approximately halving the emitted fan beam is utilized, this "precollimator" will be located at different positions in FIGS. 12 and 13 because the detectors are in different positions. Two such collimators can be provided in a bimodal system with manual replacement when a mode shift occurs, or alternatively, automatic shifting means can be provided to shift the collimators.

A CT scanner as shown in FIG. 12 or 13, with a reduced array of detectors 3 and an X-ray source 1 with at least two distinct point sources of radiation, can achieve satisfactory spatial resolution (i.e., can satisfy the Nyquist criterion). This is because X-ray source 1 can be caused to alternately emit radiation from its at least two distinct point sources of radiation. This doubles the sampling frequency and yields a two-fold improvement in spatial resolution over that achievable in a conventional rotate-rotate CT scanner having an X-ray tube with a single point source of radiation combined with a reduced array of detectors. In other words, although conventional rotate-rotate CT scanners can, even after reducing the number of detectors, still reconstruct an image based upon 360° of data, the image will have decreased spatial resolution because, in such scanners, spatial resolution is sample-frequency bound. Moreover, quarter-ray offset of the gantry iso-center is not available in conventional rotate-rotate scanners with a reduced arc of detectors to increase spatial resolution because, conventionally, this offset technique requires a full arc of detectors subtending the entire reconstruction circle. But, as noted above, by providing a scanner in accordance with the present invention with an X-ray source 1 having at least two distinct point sources of radiation, means for causing the distinct point sources of radiation to alternately emit radiation, and in addition, preferably, means for offsetting the iso-center of the gantry by a distance equal to one-fourth the effective detector pitch at the iso-center, the sample frequency is doubled and a two-fold improvement in spatial resolution is achieved.

Accordingly, the scanner of FIG. 12 or 13 can achieve equal spatial resolution to that of a conventional rotate-rotate scanner having a full arc of, e.g., twice as many detectors and a conventional X-ray tube with a single focal spot. It should be noted that both such scanners must rotate 360° to achieve the same spatial resolution. It should also be noted that the scanner shown in FIG. 12 or 13 will have fewer aliasing artifacts resulting from patient motion because the time duration between interleaved samples is milliseconds, i.e., the time between switching between distinct point sources of radiation, whereas the time duration between interleaved samples in conventional scanners is seconds because interleaving to acquire the additional data only occurs after the gantry has rotated through 180°.

Figure 14:
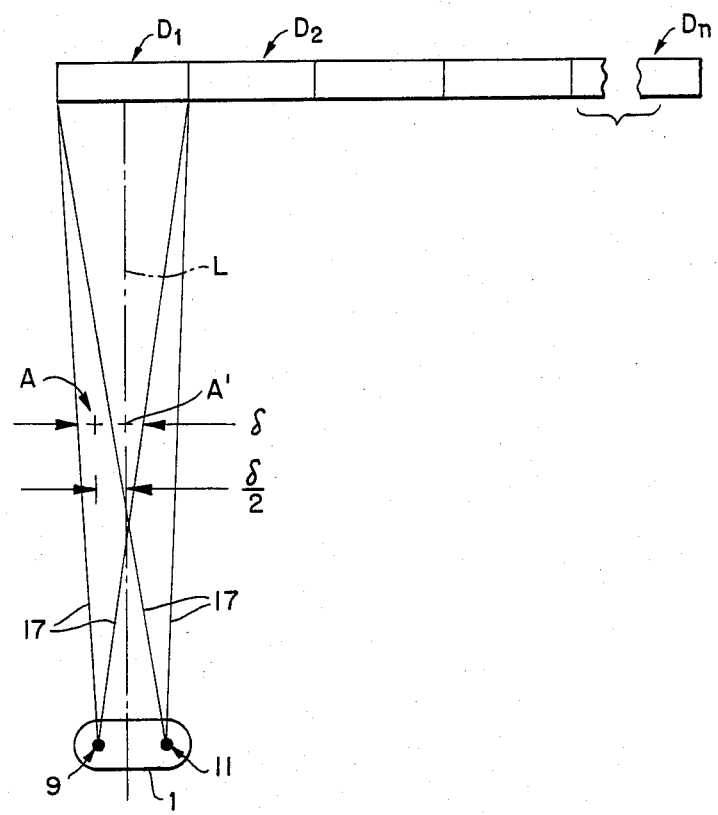
FIG. 14 illustrates a CT scanner having its iso-center offset.

FIG. 14 illustrates a system in which the gantry iso-center is offset by a distance "δ/2" equal to one-fourth the effective detector pitch at iso-center. FIG. 14 is similar to FIG. 12 except in FIG. 14 detector array 3 is disposed such that iso-center "A" is offset a distance equal to one-half the beam width at iso-center from a line "L" defined by the center of detector D₁ (which is positioned substantially diametrically opposed to X-ray source 1 on the gantry) and a point midway between the two distinct point sources of radiation 9 and 11 in X-ray source 1, or at the midpoint of whatever number of distinct point sources are provided in X-ray source 1. The position of the iso-center for the scanner of FIG. 12 is shown at "A" in FIG. 14 so that it is seen that detector array 3 has been offset to the right by a distance equal to one-half the beam width at iso-center from the position of detector array 3 in FIG. 12. Similar geometrical relationships exist with respect to systems in which one-eighth ray offset of the gantry iso-center is provided. As used above, the term "beam width" at iso-center is defined as the width of the X-ray beam traveling from the focal spot to a given detector.

FIG. 15 illustrates an X-ray tube 10 with deflection means for deflecting an electron beam from a cathode 15 having a single filament 29 onto a rotating anode 19. A continuous or intermittent beam of electrons from the filament 29 may be switched alternately between two or more focal spots 21 and 23 spaced appropriately apart on rotating anode 19. The switching is achieved by controlling the voltage applied to deflection plates 25 and 27. The switching between focal spots can be achieved by other means and still come within the spirit and scope of the present invention.

Although the preferred embodiment of the invention is a rotate-rotate CT scanner employing a rotating anode X-ray tube, a stationary anode tube is an alternative embodiment. Further, an X-ray tube having two filaments each floating with respect to the cathode cup where each filament is separately pulsed relative to the cathode alternately to effectively shift back and forth the apparent focal spot could also be utilized. Also, a plurality of X-ray tubes could be used to provide plural focal spots. In addition, two X-ray tubes each having grid control could be provided. Point sources of radiation 9 and 11 shown in FIG. 4 can illustrate alternately either a single source having dual filaments or a pair of X-ray sources. Also, the electron beam could be deflected using magnetic means to achieve the multiple focal spots.

Moreover, while the preferred utilization of the present invention is in the context of a rotate-rotate scanner, the invention can also be incorporated in other generations or types of scanners, e.g., translate-rotate, rotate-stationary (with or without nutation of the detector ring) or fully stationary plural-source strobed systems, to achieve greater sampling density and improved spatial resolution.

From the foregoing description, one skilled in the art can easily ascertain the essential characteristics of the present invention and, without departing from the spirit and scope thereof, can make various changes and modifications of the invention to adapt it to various usages and conditions.

We claim:

1. An apparatus for providing a tomographic image of a body with sampling data from said body obtained using penetrating radiation such as X-ray radiation said apparatus comprising:
    (a) a source of said penetrating radiation for transmitting radiation through a said body, said source including at least said two distinct point sources of said radiation each providing beams of said radiation;
    (b) detector means coupled to said source for detecting said radiation emitted from all of said at least two distinct point sources after passage of the radiation through the body, said detector means comprising a plurality of individual detectors arrayed within said beams;
    (c) a rotatable gantry on which said source and said detector means are mounted;
    (d) means for angularly displacing said gantry for causing the radiation emitted by said source to traverse a plurality of paths through the body and to be detected by said detector means to provide said sampling data;
    (e) means for causing said at least two distinct point sources of radiation to alternately emit radiation during said angular displacements to increase said sampling data density by providing data at intervals of no more than one half the pitch of said arrayed individual detectors to thereby provide at least two samples per beam; and
    (f) means for processing detected radiation having the increased sampling data density to provide increased spatial resolution in the tomographic images.

2. The apparatus as recited in claim 1 wherein said detector means comprises a plurality of individual detectors disposed substantially uniformly along an arc on said gantry, and said means for causing said at least two point sources of radiation to alternately emit radiation comprises means for causing said point sources to alternately emit radiation at a frequency whose period is substantially equal to the time required for said gantry to rotate through the detector pitch.

3. The apparatus as recited in claim 1 wherein said detector means comprises a plurality of individual detectors disposed substantially uniformly along an arc on said gantry, and said means for causing said point sources of radiation to alternately emit radiation is adapted to cause said point sources to alternately emit radiation at a frequency whose period is substantially equal to the time required for said gantry to rotate through the detector pitch multiplied by N, where N=2, 4, 8, 16 . . . .

4. The apparatus as recited in claim 1 wherein said at least two point sources of radiation are separated by a predetermined distance, said predetermined distance being approximately equal to $R_s/R_d \times P(N+1/n)$ where $R_s$=the distance from said source mounted on said gantry to the iso-center of said rotatable gantry, $R_d$=the distance from each of said detectors to said iso-center, P=the detector pitch, n=the number of distinct point sources of radiation and N=0, 1, 2 . . . .

5. The apparatus as recited in claim 1 wherein said source includes a target electrode for emitting radiation in response to a beam of electrons impinging thereon, and deflection means for deflecting said electron beam between at least two distinct focal spots on said target electrode.

6. The apparatus cited in claim 1 wherein said source emits a fan beam radiation, and further comprising post-patient collimator means for reducing the width of said radiation beam which is detected by said detector means, and means for further increasing the sampling density.

7. The apparatus as recited in claim 6 wherein said means for further increasing the sampling density includes at least three distinct point sources of radiation in said source.

8. The apparatus as recited in claim 6 wherein said means for said further increasing the sampling density includes said array of individual detectors disposed substantially uniformly to form an arc on said gantry, said collimator means comprising a corresponding plurality of collimators, the center of each collimator being aligned with the center of one of said individual detectors, and means for off-setting the iso-center of said gantry by a distance equal one-eighth the effective pitch of said detectors of said iso-center.

9. The apparatus as recited in claim 6 wherein said means for further increasing the sampling density includes said array of individual detectors disposed substantially uniformly along an arc on said gantry, said collimator means comprising a corresponding plurality of collimators, each collimator being off-set from the center of a said detector by one-eighth the effective detector pitch and further comprising means for off-setting iso-center of the gantry rotation by a distance equal to one-fourth the effective detector pitch at said iso-center.

10. An apparatus for examining a body by means of penetrating radiation such as X-ray radiation comprising:
(a) a source of penetrating radiation for transmitting radiation through a body, said source including at least two distinct points sources of radiation;
(b) said source comprising means for emitting a fan beam of radiation from each of said at least two point sources of radiation, each said fan beam having an apical angle $\alpha$ which is less than the apical angle $\beta$ which defines the reconstruction circle;
(c) detector means for detecting said radiation after passage through the body;
(d) means for causing radiation emitted by said source to traverse a plurality of paths through the body and to be detected by said detector means;
(e) means for causing said at least two distinct sources of radiation to alternately emit radiation; and
(f) a rotatable gantry on which said source and said detector means are mounted, and wherein said means for causing radiation emitted by said source to traverse a plurality of paths comprises means for angularly displacing said gantry.

11. The apparatus as recited in claim 10 wherein $\alpha$ is approximately one-half of $\beta$.

12. The apparatus as recited in claim 10 wherein $\alpha$ is approximately in the range of 15° to 30°.

13. The apparatus as recited in claim 10 wherein said detector means comprises a plurality of individual detectors disposed on an arc which subtends said apical angle $\alpha$, and wherein one said individual detector at the end of said arc is substantially diametrically opposed with respect to said source on said gantry.

14. The apparatus as recited in claim 13 further comprising means for offsetting the iso-center of rotation of said gantry with respect to said source and said detectors by a distance equal to one-fourth the effective detector pitch at said iso-center.

15. The apparatus as recited in claim 10 wherein said means for causing said point sources of radiation to alternately emit radiation is adapted to cause said point sources to alternately emit radiation at a frequency whose period is substantially equal to the time required for said gantry to rotate through the detector pitch.

16. The apparatus as recited in claim 10 wherein said means for causing said point sources of radiation to alternately emit radiation is adapted to cause said point sources to alternately emit radiation at a frequency whose period is substantially equal to the time required for said gantry to rotate through the detector pitch multiplied by N, where N=2, 4, 8, 16 . . . .

17. The apparatus as recited in claim 10 wherein said at least two point sources of radiation are separated by a predetermined distance, said predetermined distance being approximately equal to $R_s/R_d \times P(N+1/n)$ where $R_s$=the distance from said X-ray source mounted on said gantry to the iso-center of said rotatable gantry, $R_d$=the distance from each of said individual detectors to said iso-center, P=the detector pitch, n=the number of distinct point sources of radiation and N=0, 1, 2 . . .

18. The apparatus as recited in claim 10 wherein said source includes a target electrode for emitting radiation in response to a beam of electrons impinging thereon, and deflection means for deflecting said electron beam between at least two distinct focal spots on said target electrode.

19. The apparatus as recited in claim 10 wherein said source comprises at least two X-ray tubes, each X-ray tube comprising a distinct point source of radiation.

20. The apparatus as recited in claim 10 wherein said source comprises an X-ray tube having at least two filaments, each filament comprising a distinct point source of radiation.

21. The apparatus as recited in claim 18, 19 or 20 wherein said source includes a stationary anode.

22. The apparatus as recited in claim 18, 19 or 20 wherein said source includes a rotating anode.

23. The apparatus as recited in claim 10 wherein said detector means comprises a plurality of individual detectors disposed on an arc which subtends said apical angle α, said arc being substantially symmetrically disposed with respect to the iso-center of said gantry.

24. The apparatus as recited in claim 23 further comprising collimator means for reducing the width of a radiation beam which is detected by said detector means.

25. The apparatus as recited in claim 24 wherein said collimator means comprises high-resolution collimator means.

26. The apparatus as recited in claim 25 wherein said high-resolution collimator means includes a pin collimator.

27. The apparatus as recited in claim 24 wherein said source includes at least three distinct point sources of radiation.

28. The apparatus as recited in claim 24 wherein said plurality of individual detectors are disposed substantially uniformly along said arc on said gantry, said collimator means comprises a corresponding plurality of collimators, the center of each collimator being aligned with the center of a said detector, and further comprising means for offsetting the iso-center of said gantry by a distance equal to one-eighth the effective pitch of a said detector at said iso-center.

29. The apparatus as recited in claim 24 wherein said plurality of detectors are disposed substantially uniformly along said arc on said gantry, said collimator means comprises a corresponding plurality of collimators, the center of each collimator being offset from the center of a said detector by one-eighth the detector pitch, and further comprising means for offsetting the iso-center of the gantry rotation by a distance equal to one-fourth the effective detector pitch at said iso-center.

30. The apparatus as recited in claim 10 wherein said detector means comprises a plurality of individual detectors disposed on an arc on said gantry which subtends said apical angle α and further comprising means for displacing said plurality of individual detectors on said gantry.

31. The apparatus as recited in claim 30 wherein said means for displacing comprises means for displacing said detectors between a first position at which said detectors are asymmetrically disposed with respect to said iso-center and a second position at which said detectors are symmetrically disposed with respect to said iso-center.

32. In a rotate-rotate CT scanner having a source of pentetrating radiation for transmitting, radiation through a substantially planar section of a body, said source being mounted on a gantry for rotation and including at least two distinct point sources of radiation beams, detector means mounted on said gantry, means for angularly displacing said source and said detector means about the body to cause the radiation beams to traverse a the plurality of coplanar paths in said section, said detector means including a plurality of individual detectors disposed substantially uniformly along an arc on said gantry to detect radiation beams from all of said distinct point sources after passage through the body; a method of improving the spatial resolution of images constructed by said scanner, said method comprising the steps of:
  (a) increasing the sampling density by interleaving radiation beams between adjacent radiation beams continuously as said radiation source and said detector means are rotated about the body;
  (b) said step of increasing the sampling density comprising alternately emitting radiation from each of said at least two point sources of radiation as said radiation source and said detector means are rotated about said body; and
  (c) processing the detected radiation of increased sampling density to provide increased spatial resolution.

33. The method as recited in claim 32 including the step of alternately emitting radiation from each of said at least two point sources at a frequency whose period is substantially equal to the time required for said gantry to rotate through the detector pitch.

34. The method as recited in claim 33 wherein said period is multiplied by N, where N=2, 4, 8, 16 . . . .

* * * * *